US009027193B2

(12) United States Patent
Xi et al.

(10) Patent No.: US 9,027,193 B2
(45) Date of Patent: May 12, 2015

(54) ORAL CARE IMPLEMENT

(75) Inventors: Wen Jin Xi, Shanghai (CN); Liu Yu, Yangzhou (CN); Jian Rong Zhou, Yangzhou (CN)

(73) Assignee: Colgate-Palmolive Company, New York, NY (US)

( * ) Notice: Subject to any disclaimer, the term of this patent is extended or adjusted under 35 U.S.C. 154(b) by 23 days.

(21) Appl. No.: 13/992,263

(22) PCT Filed: Dec. 21, 2010

(86) PCT No.: PCT/CN2010/002108
§ 371 (c)(1),
(2), (4) Date: Jun. 7, 2013

(87) PCT Pub. No.: WO2012/083488
PCT Pub. Date: Jun. 28, 2012

(65) Prior Publication Data
US 2013/0255020 A1    Oct. 3, 2013

(51) Int. Cl.
*A46B 9/06*    (2006.01)
*A46B 9/04*    (2006.01)
*A46B 3/22*    (2006.01)
*A46B 7/06*    (2006.01)
*A46B 15/00*   (2006.01)
*A46B 3/00*    (2006.01)
(Continued)

(52) U.S. Cl.
CPC ... *A46B 9/04* (2013.01); *A46B 3/22* (2013.01); *A46B 7/06* (2013.01); *A46B 15/0081* (2013.01); *A46B 2200/1026* (2013.01); *A46B 2200/1066* (2013.01); *A46B 3/00* (2013.01); *A46B 9/06* (2013.01); *A61C 17/00* (2013.01); *A46B 5/0029* (2013.01)

(58) Field of Classification Search
USPC ......... 15/110, 167.1, 187, 188, 201; 601/141; 606/161
See application file for complete search history.

(56) References Cited

U.S. PATENT DOCUMENTS 1,840,246 A    1/1932  Newman
1,860,924 A    5/1932  Cooke
(Continued)

FOREIGN PATENT DOCUMENTS

WO    WO00/64307    11/2000

OTHER PUBLICATIONS

International Search Report and the Written Opinion of the International Searching Authority issued in International Application PCT/CN2010/002108 mailed Oct. 13, 2011.

*Primary Examiner* — Mark Spisich
(74) *Attorney, Agent, or Firm* — Ryan M. Flandro

(57) ABSTRACT

An oral care implement, such as a toothbrush, comprising a flexible head formed of a plurality of flexibly connected segments. In one embodiment, the invention can be an oral care implement comprising a handle and a head. The head can be formed by a plurality of spaced-apart segments constructed of a rigid material and separated by a channel containing an elastomeric material. An elastomeric cleaning element comprising, a base portion and an upper portion extends form a front surface of the head. The elastomeric cleaning element extends from and is connected to the elastomeric material of the channel so that the base portion overlies a portion of each of the front surfaces of the segments on opposing sides of the channel. In another embodiment, the invention can be the elastomeric cleaning element itself, irrespective of the type of head in which it is incorporated. In yet another embodiment, the base portion can be tapered.

35 Claims, 15 Drawing Sheets

(51) Int. Cl.
*A61C 17/00* (2006.01)
*A46B 5/00* (2006.01)

(56) References Cited

U.S. PATENT DOCUMENTS

| | | | |
|---|---|---|---|
| 2,065,584 A * | 12/1936 | Hempel | 15/188 |
| 2,088,839 A * | 8/1937 | Coney et al. | 15/167.1 |
| 2,438,268 A | 3/1948 | Bressler | |
| 2,637,870 A * | 5/1953 | Cohen | 15/188 |
| 2,650,383 A | 9/1953 | Bressler | |
| 2,676,350 A | 4/1954 | Bressler | |
| 2,917,057 A * | 12/1959 | Busseuil | 401/129 |
| 3,188,672 A | 6/1965 | Gary | |
| 3,253,292 A | 5/1966 | Herschensohn | |
| 3,633,237 A * | 1/1972 | Bagube | 15/188 |
| 4,566,145 A | 1/1986 | Wachtel | |
| 5,651,158 A | 7/1997 | Halm | |
| 5,802,656 A | 9/1998 | Dawson et al. | |
| 5,926,900 A * | 7/1999 | Bennett | 15/167.1 |
| 5,946,759 A | 9/1999 | Cann | |
| 5,970,564 A | 10/1999 | Inns et al. | |
| 5,991,959 A | 11/1999 | Raven et al. | |
| 6,178,582 B1 * | 1/2001 | Halm | 15/167.1 |
| 6,463,618 B1 | 10/2002 | Zimmer | |
| 6,725,493 B2 * | 4/2004 | Calabrese et al. | 15/110 |
| 6,996,870 B2 * | 2/2006 | Hohlbein | 15/110 |
| 7,024,720 B2 | 4/2006 | Moskovich et al. | |
| 7,143,462 B2 | 12/2006 | Hohlbein | |
| 7,322,067 B2 | 1/2008 | Hohlbein | |
| 7,707,676 B2 | 5/2010 | Solanki | |
| 7,707,677 B2 | 5/2010 | Moskovich et al. | |
| 7,721,376 B2 | 5/2010 | Hohlbein et al. | |
| 7,845,042 B2 | 12/2010 | Moskovich et al. | |
| 7,975,343 B2 | 7/2011 | Hohlbein et al. | |
| 8,032,971 B2 | 10/2011 | Moskovich | |
| 8,056,176 B2 | 11/2011 | Claire-Zimmet et al. | |
| 8,151,397 B2 | 4/2012 | Moskovich et al. | |
| 2003/0084533 A1 | 5/2003 | Gelder et al. | |
| 2004/0158948 A1 * | 8/2004 | Sander et al. | 15/188 |
| 2005/0210612 A1 | 9/2005 | Hohlbein et al. | |
| 2006/0117508 A1 | 6/2006 | Hohlbein | |
| 2007/0163064 A1 | 7/2007 | Wong et al. | |
| 2007/0204417 A1 | 9/2007 | Russell et al. | |
| 2008/0052848 A1 | 3/2008 | Hohlbein | |
| 2008/0115305 A1 | 5/2008 | Battaglia | |
| 2008/0307596 A1 | 12/2008 | Hohlbein | |
| 2010/0229316 A1 | 9/2010 | Hohlbein et al. | |

* cited by examiner

US 9,027,193 B2

ORAL CARE IMPLEMENT

CROSS-REFERENCE OF RELATED APPLICATIONS

This application is a U.S. national stage entry under 35 U.S.C. §371 of Patent Cooperation Treaty Patent Application No. PCT/CN2010/002108, filed Dec. 21, 2010, the entirety of which is incorporated herein by reference.

FIELD OF THE INVENTION

The present invention relates to oral care implements, and specifically to oral care implements having a flexible head formed by a plurality of segments and/or a specially designed elastomeric cleaning element.

BACKGROUND OF THE INVENTION

A toothbrush is used to clean the teeth by removing plaque and debris from the tooth surfaces. Conventional toothbrushes having a flat bristle trim are limited in their ability to conform to the curvature of the teeth, to penetrate into the interproximal areas between the teeth, to sweep away the plaque and debris, and to clean along the gum line. Additionally, such toothbrushes have a limited ability to retain dentifrice for cleaning, the teeth. During the brushing process, the dentifrice typically slips through the tufts of bristles and away from the contact between the bristles and the teeth. As a result, the dentifrice is often spread around the mouth, rather than being concentrated on the contact of the bristles with the teeth. Therefore, the efficiency of the cleaning process is reduced.

While substantial efforts have been made to modify the cleaning elements of toothbrushes to improve the efficiency of the oral cleaning process, the industry continues to pursue arrangements of cleaning elements that will improve upon the existing technology.

A number of attempts have been made to create flexible toothbrush heads that provide greater cleaning efficacy by allowing the head to flex, thereby allowing the bristles and other tooth cleaning elements to extend at various angles relative to one another. In one type of known flexible toothbrush head, the head is broken up into a plurality of segments that are flexible relative to one another and relative to the handle. However, the existing designs of many segmented toothbrush beads result in the head having either too much or not enough flexibility. Too much flexibility results in the head being unable to transmit sufficient pressure to the teeth or other oral surfaces via the bristles when the handle is subject to normal brushing forces. On the other hand, inadequate flexibility results in the segments (and thus the bristles) remaining substantially stationary, thereby defeating the purpose of having a flexible head.

More recently, the strategic arrangement and combination of tooth cleaning elements in the form of elastomeric cleaning elements and bristle tufts has become a more common way of improving cleaning efficiency. However, very little efforts have been made to coordinate the structure and arrangement of elastomeric cleaning elements on flexible toothbrush heads formed by a plurality of segments.

Elastomeric soft tissue cleaners, which are typically located on the rear surface of the toothbrush head, have also become quite popular. However, as with the tooth cleaning elements, very little effort has been expended to coordinate the structure of the soft tissue cleaner with the structure of flexible toothbrush heads utilizing a plurality of segments.

BRIEF SUMMARY OF THE INVENTION

The present invention is directed to an oral care implement. In one aspect, the invention can be an oral care implement comprising a handle and a head. The head can be formed by a plurality of spaced-apart segments constructed of a rigid material and separated by a channel containing an elastomeric material. An elastomeric cleaning element comprising a base portion and an upper portion extends form a front surface of the head. The elastomeric cleaning element extends from and is connected to the elastomeric material of the channel so that the base portion overlies a portion of each of the front surfaces of the segments on opposing sides of the channel. In another aspect, the invention can be the elastomeric cleaning element itself, irrespective of the type of head with which it is incorporated. In yet another aspect, the base portion may be tapered.

In one embodiment, the invention can be an oral care implement comprising: a handle; a head connected to the handle, the head formed by a plurality of segments constructed of a rigid material, the plurality of segments including a first segment and a second segment, each of the first and second segments comprising a front surface, wherein the first and second segments are spaced apart so that a channel exists between the first and second segments; an elastomeric material in the channel connecting the first and second segments, the first and second segments being flexible relative to one another between a normal state and a flexed state; and an elastomeric cleaning element comprising: a base portion connected to and extending from the elastomeric material disposed in the channel, the base portion overlying a portion of each of the front surfaces of the first and second segments when the first and second segments are in the normal state; and an upper portion extending from the base portion.

In another embodiment, the invention can be an oral care implement comprising: a handle; a head connected to the handle, the head formed by a plurality of segments constructed of a rigid material, the plurality of segments including a first segment and a second segment, each of the first and second segments comprising a front surface, wherein the first and second segments are spaced apart so that a channel exists between the first and second segments, the channel extending along an axis and having a width measured perpendicular to said axis; an elastomeric material in the channel connecting the first and second segments; and an elastomeric cleaning element comprising: a base portion connected to and extending from the elastomeric material disposed in the channel, the base portion extending from a lower end that overlies a portion of each of the front surfaces of the first and second segments to an upper end spaced from the front surfaces of the first and second segments; and an upper portion extending from the upper end of the base portion to a terminal end, the lower end of the base portion having a first width measured perpendicular to the axis of the channel that is greater than the width of channel, the upper end of the base portion having, a second width measured perpendicular to the axis of the channel that is less than the first width.

In yet another embodiment, the invention can be an oral care implement comprising: a handle; a head connected to the handle, the head having a front surface and at least one channel in the front surface of the head, the channel extending along an axis; and an elastomeric wall extending from the front surface of the head, the elastomeric wall comprising: a root portion disposed within the channel; a tapered base portion connected to and extending from the root portion, the tapered base portion overlying portions of the front surface of the head on opposite sides of the channel; and an upper portion extending from the tapered base portion to a terminal end.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

This invention is capable of use in a broad array of oral care implements and hygiene products. The drawings illustrate one use of the invention and are not to be construed as the only embodiment of the invention.

The present invention will become more fully understood from the detailed description and the accompanying drawings, wherein.

DETAILED DESCRIPTION OF THE INVENTION

The following description of the preferred embodiment(s) is merely exemplary in nature and is in no way intended to limit the invention, its application, or uses.

In the following description, the invention is discussed in terms of a manual toothbrush incorporating the novel arrangement of cleaning elements. However, in other forms, the invention could be in the form of other oral care implements including a soft-tissue cleansing implement, a powered toothbrush, or other ansate implement designed for oral care.

Figure 1:
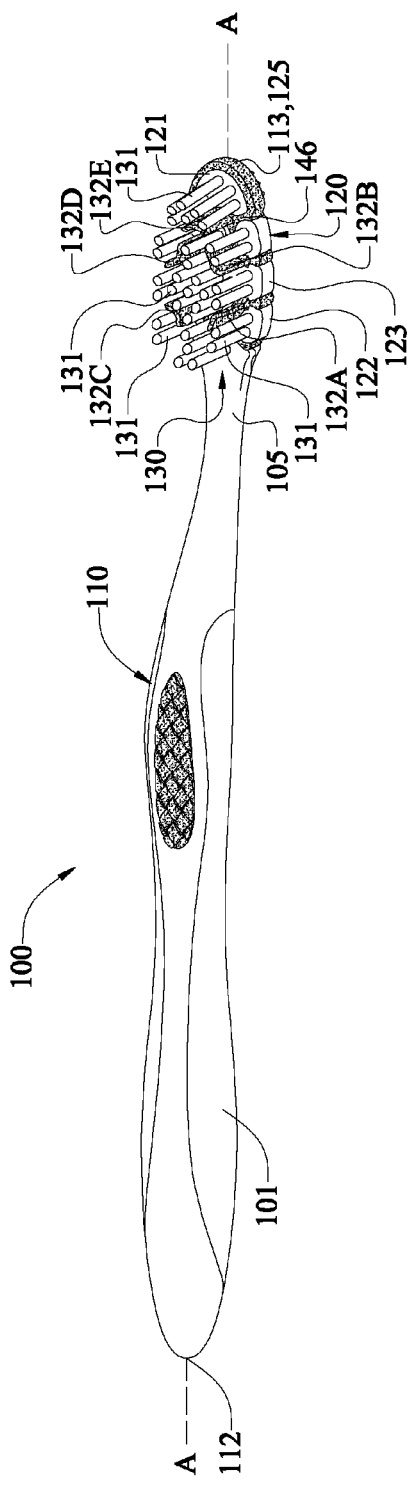
FIG. 1 is a front perspective view of an oral care implement, in the form of a toothbrush, according to one embodiment of the present invention.
Figure 2:
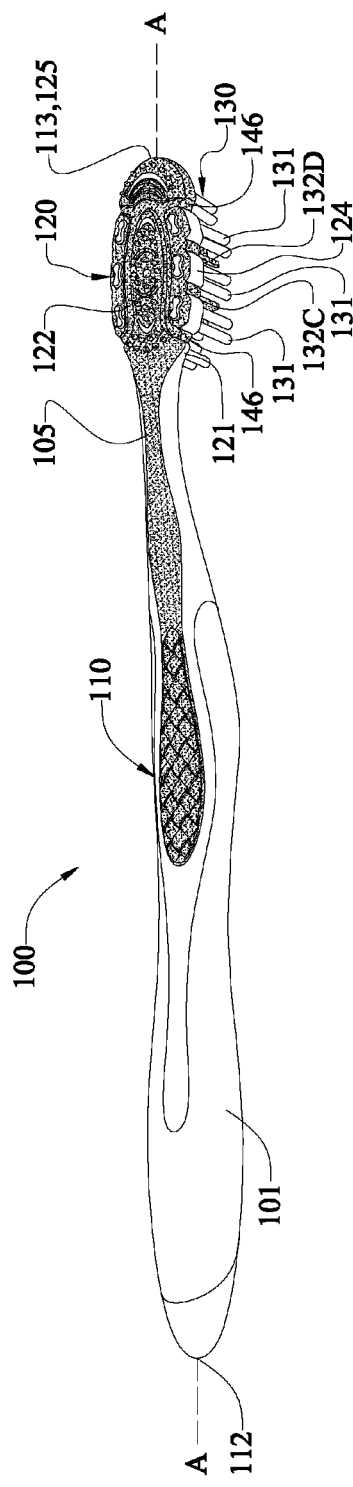
FIG. 2 is a rear perspective view of the toothbrush of FIG. 1.

Referring first to FIGS. 1-2, a toothbrush 100 is illustrated according to one embodiment of the present invention. The toothbrush 100 generally comprises a handle 110 and a head 120. The handle 110 provides the user with a mechanism by which he/she can readily grip and manipulate the toothbrush 100. The handle 110 may be formed of many different shapes, sizes, materials and by a variety of manufacturing methods that are well-known to those skilled in the art. If desired, the handle 110 may include a suitable textured grip 101 made of elastomeric material or can be a multi-part construction. Stated simply, unless specifically stated otherwise, the details of the handle 110 are not limiting of the present invention and, thus, require no further discussion for purposes of the present invention.

The toothbrush 100 extends from a proximal end 112 to a distal end 113 along a longitudinal axis A-A, a portion of which forms the longitudinal axis of the head 120. The head 120 is connected to a distal end 105 of the handle 110. As discussed in greater detail below, the skeleton of the head 120 is integrally formed with the handle 110 in certain embodiments of the invention thereby forming a single unitary structure. An injection molding, milling, machining or other suitable process can be used as is known in the art. However, in other embodiments, the handle 110 and the head 120 may be formed as separate components which are operably connected at a later stage of the manufacturing process by any suitable technique known in the art, including without limitation thermal welding, a tight-fit assembly, a coupling, sleeve, adhesion, or fasteners. Whether the head 120 and handle 110 are of a unitary or multi-piece construction (including, connection techniques) is not limiting of the present invention in all embodiments.

It should be noted at this time that relative terms such as distal, middle, proximal, upper, lower, top, bottom, left, right etc., are merely used to delineate relative positions of the components of the toothbrush 100 with respect to one another and are not intended to be in any further way limiting of the present invention.

The head 120 generally comprises a front surface 121 and a rear surface 122. The front surface 121 and the rear surface 122 of the head 120 can take on a wide variety of shapes and contours, none of which are limiting of the present invention. For example, the front and rear surfaces 121, 122 can be planar, contoured or combinations thereof. The head 120 also comprises a right lateral edge 123, a left lateral edge 124, and a distal edge 125, which collectively form the peripheral edge of the head 120 that connect the front and rear surfaces 121, 122. In the exemplified embodiment, the distal edge 125 is located at the distal end 113.

A plurality of cleaning elements 130 may extend from the front surface 121 of the head 120 for contacting and cleaning an oral surface, preferably teeth. While the plurality of tooth cleaning elements 130 is particularly suited for brushing teeth, the plurality of tooth cleaning elements 130 can also be used to clean other surfaces of the oral cavity if desired. As used herein, the term "tooth cleaning element" is used in a generic sense to refer to any structure that can be used to clean or massage an oral surface through relative surface contact. Common examples of "tooth cleaning elements" include, without limitation, filament bristles, fiber bristles, nylon bristles, spiral bristles, rubber bristles, elastomeric protrusions, flexible polymer protrusions, co-extruded filaments, flag bristles, crimped bristles, anti-bacterial bristles and combinations thereof and/or structures containing, such materials or combinations.

As discussed below, in the exemplified embodiment, the plurality of cleaning elements 130 comprises a plurality of bristle tufts 131 and a plurality of elastomeric cleaning elements 132A-E. In the exemplified embodiment, the elastomeric cleaning elements 132A-E are in the form of arcuate elastomeric walls. However, in certain other embodiments, the elastomeric cleaning elements 132A-E can be in the form of elastomeric fingers, linear elastomeric walls, and/or combinations thereof. The elastomeric cleaning elements 132A-E are formed of a suitable elastomeric material. In one embodiment, the elastomeric cleaning, elements 132A-E are formed of a thermoplastic elastomer ("TPE"). Other suitable elastomeric materials include any biocompatible resilient material suitable for uses in an oral hygiene apparatus. To provide optimum comfort as well as cleaning benefits, the elastomeric material preferably has a hardness property in the range of A10 to A40 Shore hardness, and preferably A25 Shore hardness. One preferred elastomeric material is styrene-ethylene/butylene-styrene block copolymer (SEBS) manufactured by GLS Corporation. Nevertheless, SEBS material from other manufacturers or other materials within and outside the noted hardness range could be used.

Figure 3:
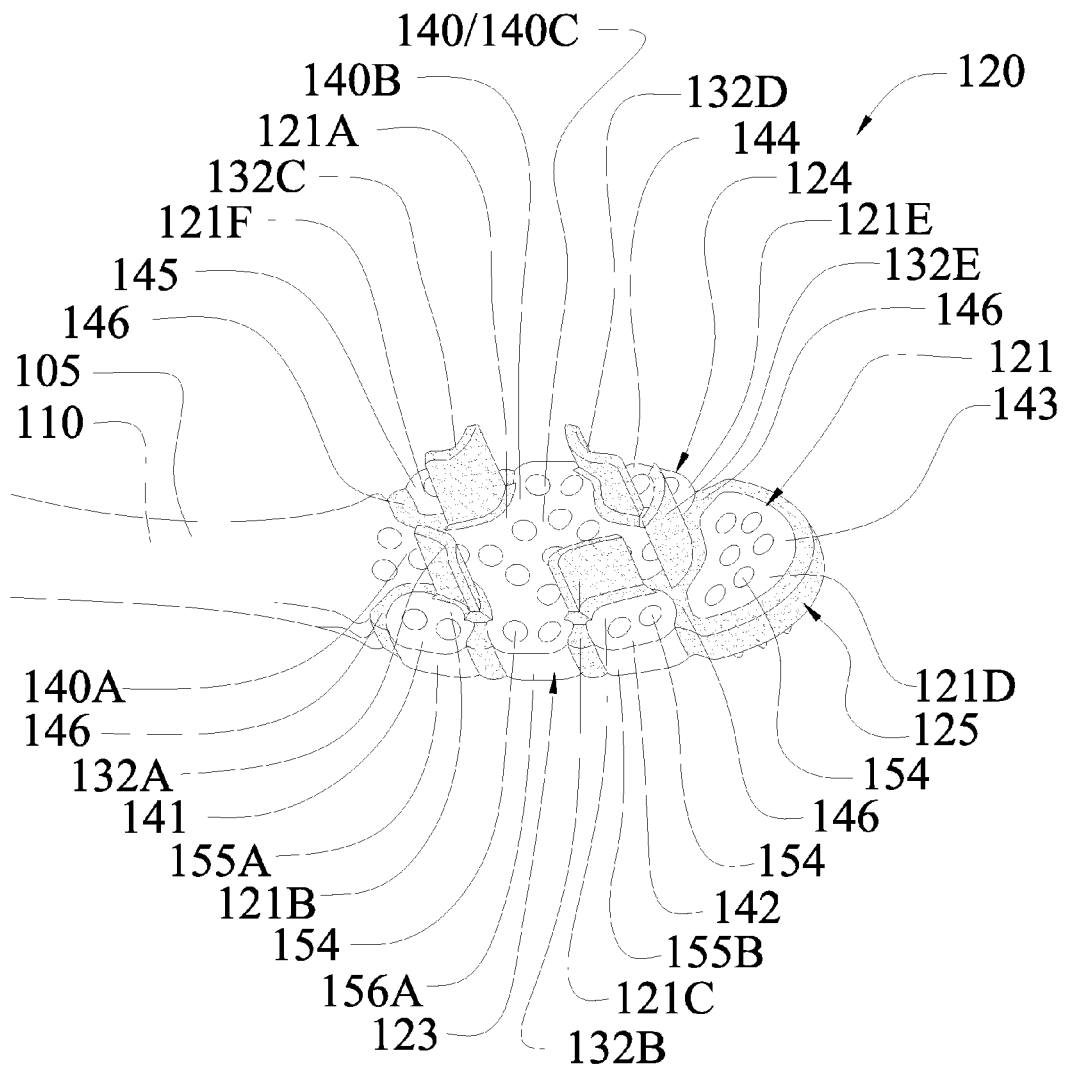
FIG. 3 is a front perspective view of the head of the toothbrush of FIG. 1 wherein the bristle tufts have been removed.
Figure 4:
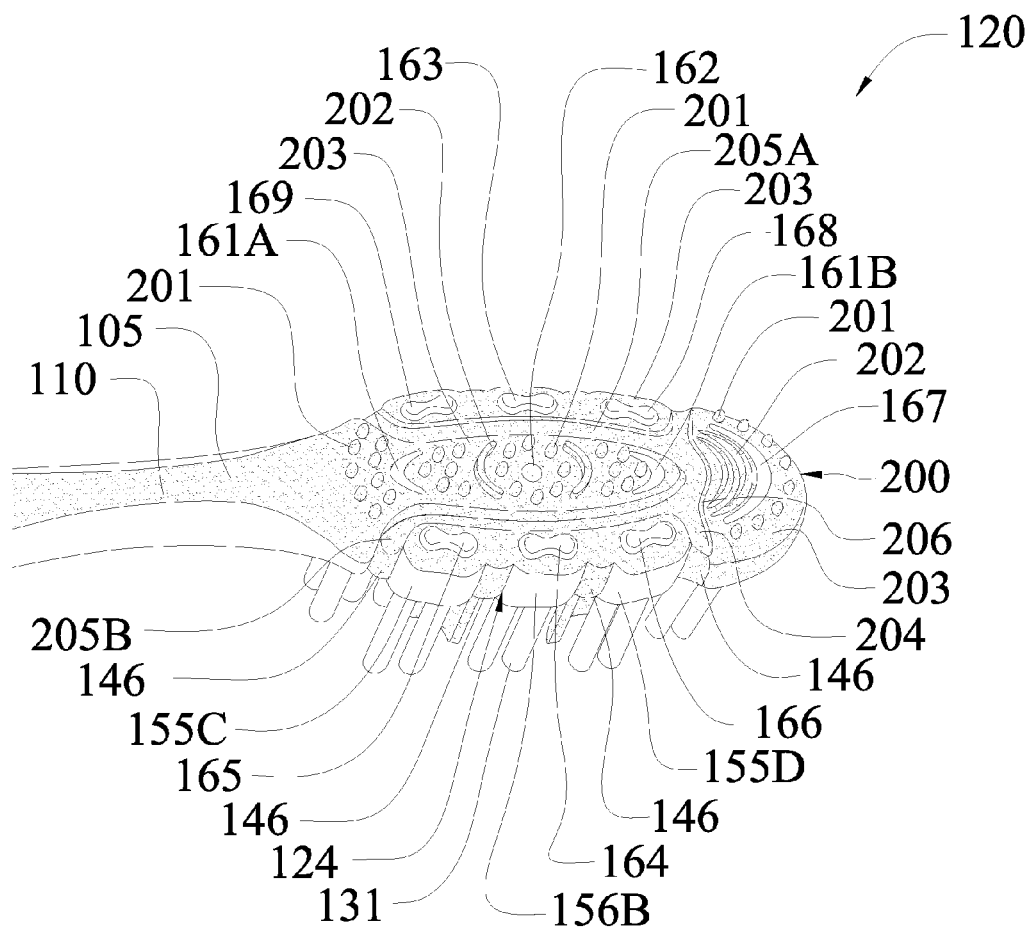
FIG. 4 is a rear perspective view of the head of the toothbrush of FIG. 1.
Figure 5:
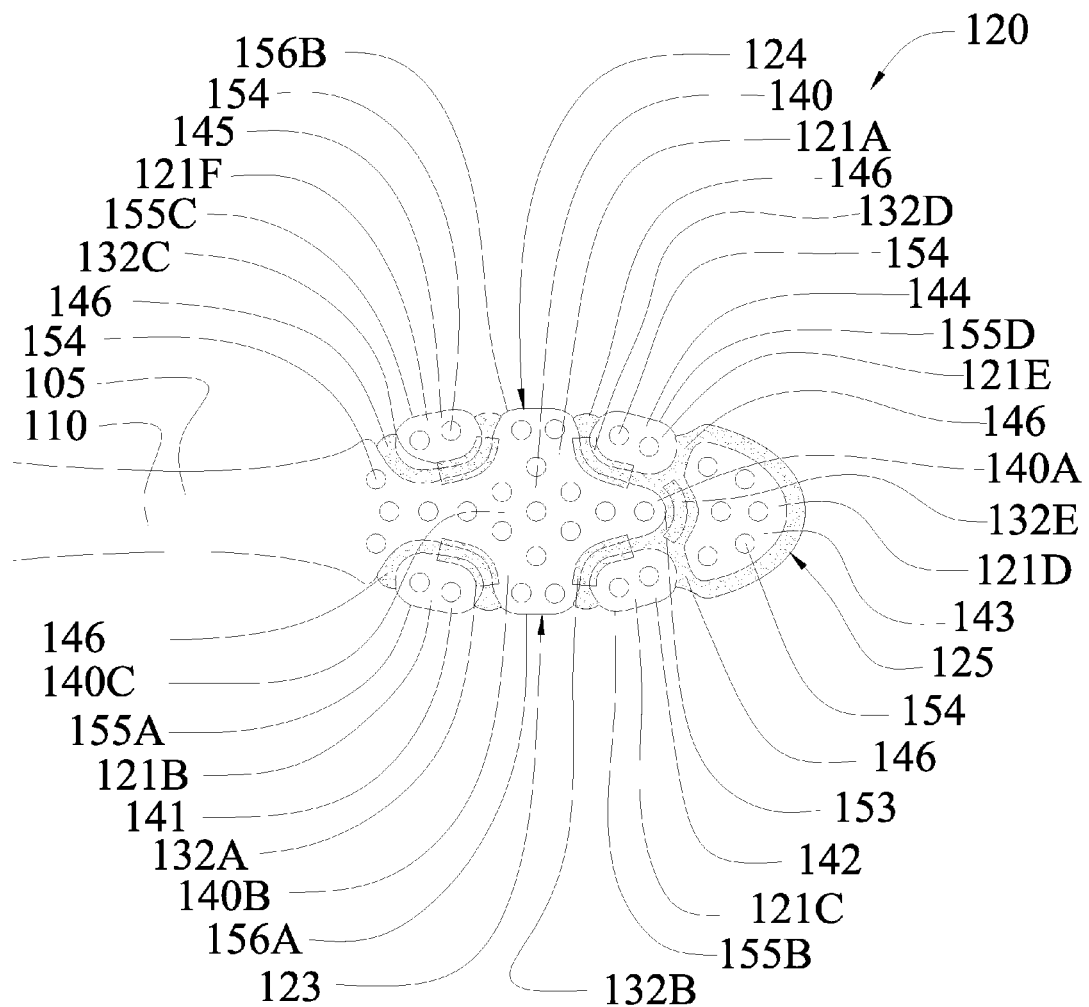
FIG. 5 is a front view of the head of the toothbrush of FIG. 1 wherein the bristle tufts have been removed.
Figure 6:
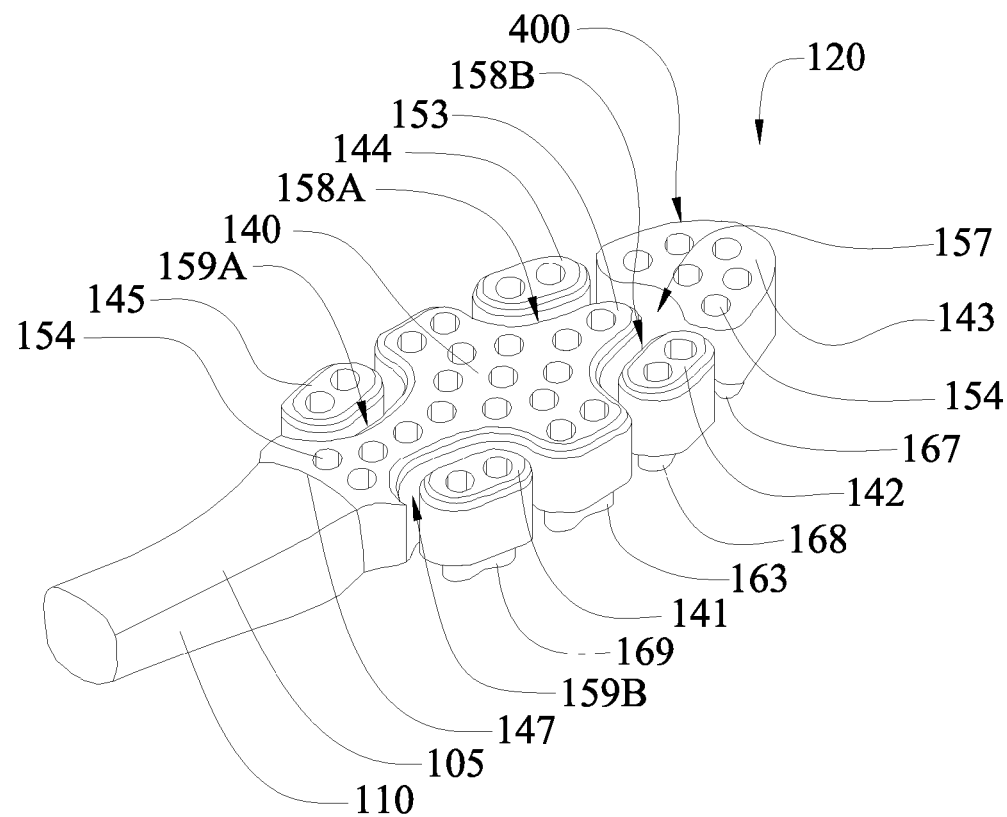
FIG. 6 is a front perspective view of the rigid material skeleton of the head of the toothbrush of FIG. 1.
Figure 7:
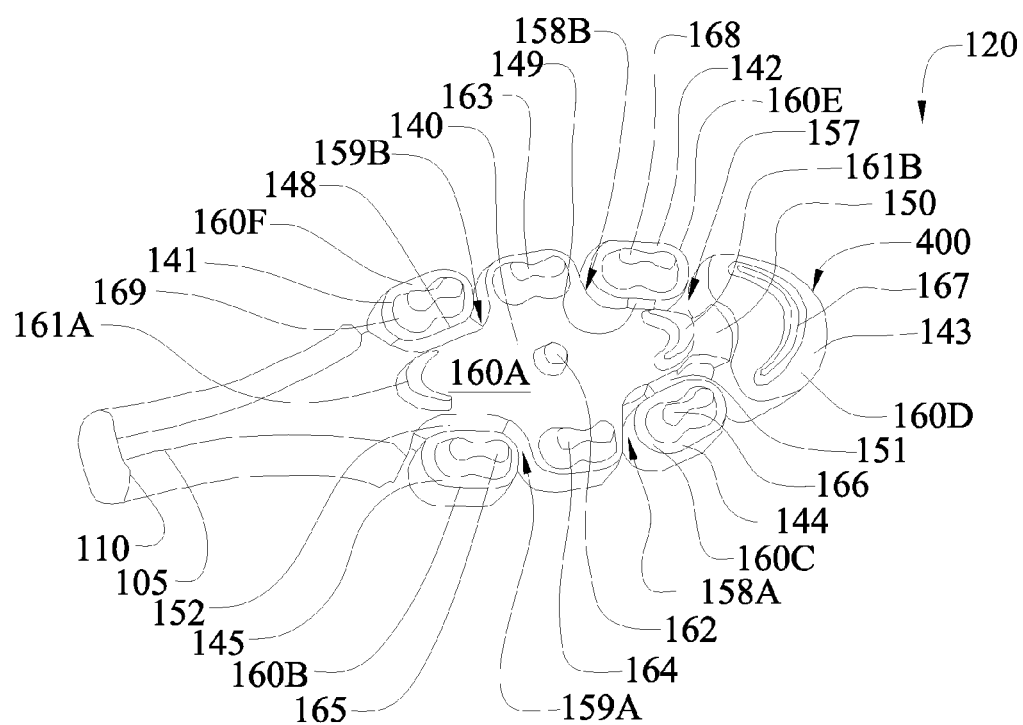
FIG. 7 is a rear perspective view of the rigid material skeleton of the head of the toothbrush of FIG. 1.
Figure 8:
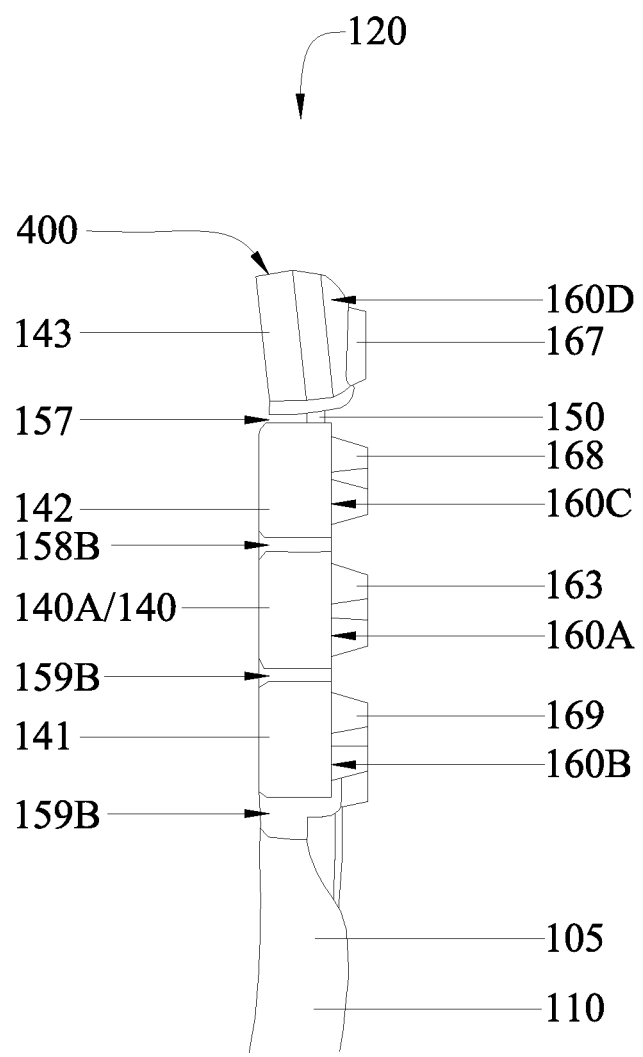
FIG. 8 is a side view of the rigid material skeleton of the head of the toothbrush of FIG. 1.
Figure 9:
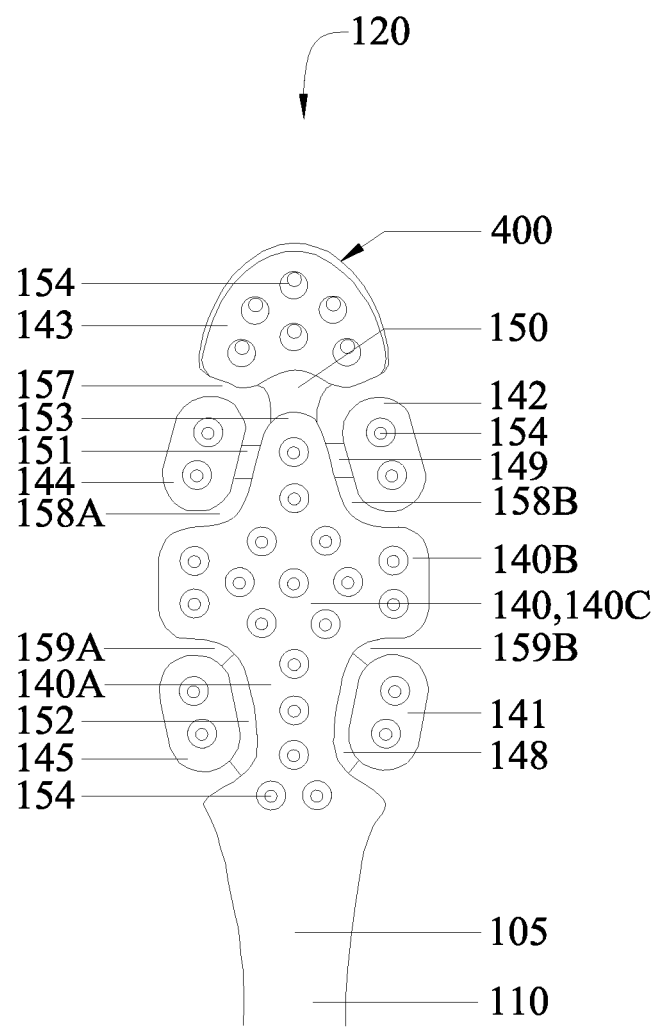
FIG. 9 is a front view of the rigid material skeleton of the head of the toothbrush of FIG. 1.
Figure 10:
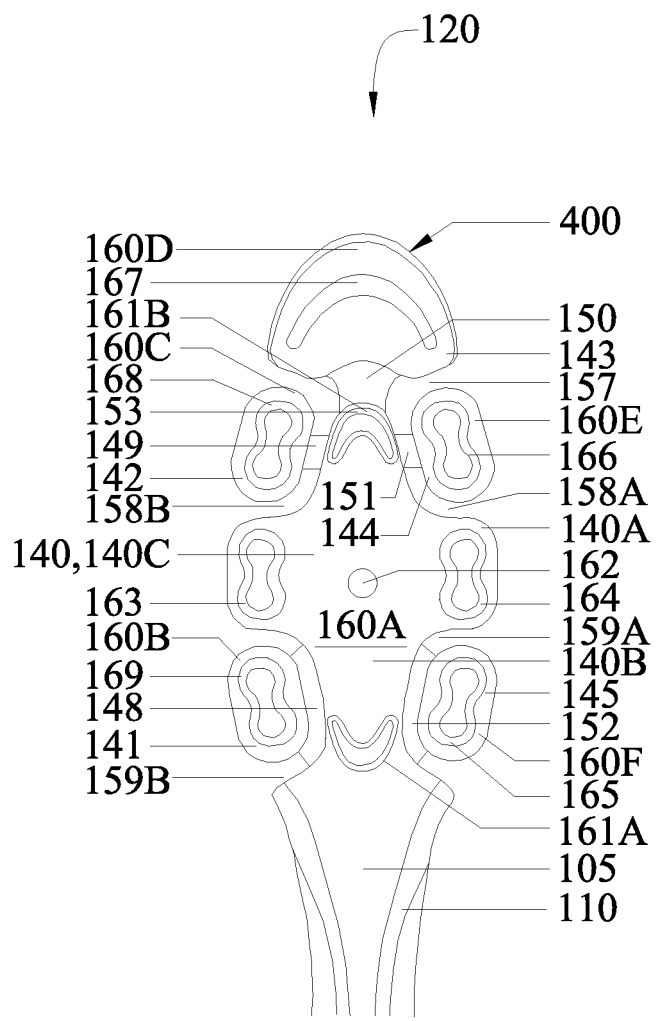
FIG. 10 is a rear view of the rigid material skeleton of the head of the toothbrush of FIG. 1.

Referring now to FIGS. 3-5 concurrently, the details of the head 120 will be described in accordance with one embodiment of the present invention. The head 120 of the toothbrush 100 extends along a longitudinal axis A-A. The head 120 generally comprises a plurality of spaced-apart segments 140-145. The plurality of segments 140-145 are constructed of a rigid material. In one embodiment, the plurality of segments 140-145 are formed of a hard plastic. Suitable hard plastics include, without limitation, polypropylene, polymers and copolymers of ethylene, propylene, butadiene, compounds and polyesters such as polyethylene terephthalate. In certain embodiments, the plurality of the segments 140-145 are formed of the same rigid material as the main structural component of the handle 110.

In the exemplified embodiment, the plurality of segments 140-145 include a central segment 140 and a plurality of peripheral segments 141-145. The central segment 140 is non-movably connected to the distal end 105 of the handle 110 in certain embodiments. For example, the central segment 140 may be integrally formed with the distal end 105 of the handle 110. In one specific embodiment, the main structural component of the handle 110 and a skeleton 400 (FIGS. 6-10) of the head 120 can be integrally formed in single injection molding step (which may use multi-ports for injecting the rigid material in liquid form).

The central segment 140 acts a hub to which the peripheral segments 141-145 are flexible connected. As discussed in greater detail below, each of the peripheral segments 141-145 are flexibly connected to the central segment 140 by an elastomeric material 146 that tills channels 157-159B (referring to FIG. 6, for example) formed between adjacent segments 140-145 and struts 148-152 that extend between the central segment 140 and the peripheral segments 141-145.

In the exemplified embodiment, the central segment 140 has a cruciform shape. Of course, the invention is not limited in all embodiments and may take on other shapes in certain other embodiments, including T-shaped, rectangular, oval, triangular, polygonal, or irregular. For purposes of discussion, the central segment 140 will be referred to as a cruciform segment 140 throughout the remainder of this written description because the exemplified embodiment is cruciform in shape. The cruciform segment 140 comprises a longitudinal portion 140A and a transverse portion 140B that intersect at a central juncture portion 140C. The longitudinal portion 140A extends along the longitudinal axis A-A in a coaxial alignment while the transverse portion 140B extends substantially perpendicular to the longitudinal axis A-A. In the exemplified embodiment, the transverse portion 140B extends the entire width of the head 120 (wherein the width of the head 120 is the distance between the right and left lateral edges 123, 124 measured substantially perpendicular to the longitudinal axis A-A) while the longitudinal portion 140A extends less than the entire length of the head 120 (wherein the length of the head 120 is the distance between a proximal end 147 of the head 120 (FIG. 6) to the distal edge 125 of the head 120 measured along the longitudinal axis A-A).

In the exemplified embodiment, the plurality of peripheral segments 141-145 comprises a distal segment 143, a first pair of segments 141, 145, and a second pair of segments 142, 144. The distal segment 143 is located at a distal end 153 of the cruciform segment 140. The first pair of segments 141, 145 are located on opposite sides of the longitudinal portion 140A of the cruciform segment 140. The second pair of segments 142, 144 are also located on opposite sides of the longitudinal portion 140A of the cruciform segment 140. However, the first pair of segments 141, 145 are located on an opposite side of a transverse portion 140B of the cruciform segment 140 than the second pair of segments 142, 144. Each of the segments 141-142, 144-145 of the first and second pairs are isolated from the cruciform segment 140 by the channels 158A-159B containing the elastomeric material 146. The distal segment 143 is also isolated from the cruciform segment 140 and the second pair of segments 142, 144 by a transverse channel 157 containing the elastomeric material 146. The various channels 157-159B will be described in greater below with respect to FIGS. 6-10.

Each of the plurality of segments 140-145 comprises a front surface 121A-121F. The front surfaces 121A-F of the segments 140-145 collectively form the front surface 121 of the head 120 in combination with the elastomeric material 146 of the channels. As will be described in greater below with respect to FIGS. 11-13, portions of the front surfaces 121A-C, 121E-F of the segments 140-142, 144-145 are covered (i.e., overlaid) by base portions of the elastomeric cleaning elements 132A-D. However, a substantial majority of the front surfaces 121A-F of the segments 140-145 remain exposed, thereby forming bristle regions from which the bristle tufts 131 extend from the segments 140-145. The rigid material of the segments 140-145 is exposed via the bristle regions and provide a sufficiently rigid structure to which the bristle tufts 131 can be secured.

Each of the segments 140-145 includes a plurality of bristle tufts 131 extending from the front surfaces 121A-F. In the exemplified embodiment, the bristle tufts 131 are secured to the segments 140-145 by anchoring the bristle tufts 131 in tuft holes 154 formed in the front surfaces 121A-F. The bristle tufts 131 can be anchored within the tuft holes 154 using staples, some welding, and other techniques known in the art. However, in alternate embodiments, the bristle tufts 131 can be secured to the segments 140-145 in any manner known in the art. For example, anchor free tufting (AFT) could be used to mount the bristle tufts 131. In AFT, a plate or membrane is secured to the segments 140-145, such as by ultrasonic welding. The bristle tufts 131 for other tooth cleaning elements) extend through the plate or membrane. The free ends of the bristle tufts 131 on one side of the plate or membrane perform the cleaning function. The ends of the bristle tufts 131 on the other side of the plate or membrane are melted together by heat to be anchored in place.

The peripheral segments 141-142, 144-145 of the first and second pairs further comprise side surfaces 155A-D. Similarly, the transverse portion 140B of the cruciform segment 140 (which is also the central segment more generally) also comprises side surfaces 156A-B. Each of the side surfaces 155A-B of the peripheral segments 141-142 and the side surface 156A of the cruciform segment 140 form a portion of the right lateral edge 123 of the head 120. Similarly, the side surfaces 155C-D of the peripheral segments 144-145 and the side surface 156B of the cruciform segment 140 form a portion of the left lateral edge 124 of the head 120. The side surfaces 155A-0 of the peripheral segments 141-142, 144-145 and the side surfaces 156A-B of the cruciform segment 140 are not covered by the elastomeric material 146 of the channels 157-159B, thereby remaining exposed.

Referring now to FIGS. 6-10 concurrently, the structure of the head 120 will be described in greater detail. In FIGS. 6-10, all of the elastomeric material 146 of the head 120 (including the elastomeric material 146 of the channels 157-159B, the elastomeric soft tissue cleaner 200, and the elastomeric cleaning elements 132A-E) has been removed, thereby exposing the skeleton 400 which is formed of the rigid material, such as a hard plastic, such as polypropylene. The skeleton 400 comprises the segments 140-145 and the struts 148-152. In one embodiment, the entirety of the skeleton 400 may be formed integrally as a unitary structure. However, in other embodiments, the components of the skeleton 400 may be formed separately and later assembled. Moreover, in certain alternative embodiments, one or all of the struts 148-152 may be omitted all together. In such an embodiment, the segments 140-145 would be flexibly connected together solely by the elastomeric material 146. Furthermore, while the exemplified embodiment of the head 120 of the present invention comprises six segments 140-145, in other embodiments, or less segments may be used as desired.

As mentioned above, the segments 140-145 of the head 120 are spaced apart from one other. As a result, adjacent segments 140-145 of the head 120 are separated by one or more of the channels 157-159B. In the exemplified embodiment, the peripheral segment 141 is isolated from the cruciform segment 140 by the channel 159B while the peripheral segment 145 is isolated from the cruciform segment 140 by the channel 159A. The channels 159A-B may be curved channels. In the exemplified embodiment, the channels 159A-B are arcuate and take on a substantially U-shape. However, it is contemplated that the channels 159A-B can take on other appropriate shapes in other embodiments.

Similarly, the peripheral segment 142 is isolated from the cruciform segment 140 by a channel 158B while the peripheral segment 144 is isolated from the cruciform segment 140 by a channel 158A. The channels 158A-B may also be curved channels. In the exemplified embodiment, the channels 158A-B are arcuate and take on a substantially J-shape. However, it is contemplated that the channels 158A-B can take on other appropriate shapes in other embodiments. For example, the channels 158A-B may take on a substantially U-shaped and a portion of each of the channels 158A-B may coincide with a portion of the transverse channel 157.

The distal segment 143 is isolated from the cruciform segment 140 by a transverse channel 157. The transverse channel 157 also isolates the distal segment 143 from second pair of peripheral segments 142, 144. The transverse channel 157 is a curved channel. In the exemplified embodiment, the transverse channel 157 takes on a generally undulating shape. Moreover, the transverse channel 157 extends across the entire width of the head 120. In other words, the transverse channel 157 extends from the right lateral edge 123 to the left lateral edge 124 of the head 120. In sonic embodiments, a portion of the transverse channel 157 may coincide with a portion of the channel 158A. Similarly, in some embodiments, a portion of the transverse channel 157 may coincide with a portion of the channel 158B.

The struts 148-152 are disposed within the channels 157-159B and connect the peripheral segment's 141-145 to the cruciform segment 140. Specifically, the strut 148 connects the segment 141 to the cruciform segment 140. The strut 149 connects the segment 142 to the cruciform segment 140. The strut 150 connects the distal segment 143 to the cruciform segment 140. The strut 151 connects the segment 144 to the cruciform segment 140. The strut 152 connects the segment 145 to the cruciform segment 140. While the foregoing description provides that one of the struts 148-152 connects one of the peripheral segments 141-145 to the cruciform segment 140, it is contemplated that more than one struts 148-152 or connection members may be used to connect the peripheral segments 141-145 to the cruciform segment 140.

Figure 12:
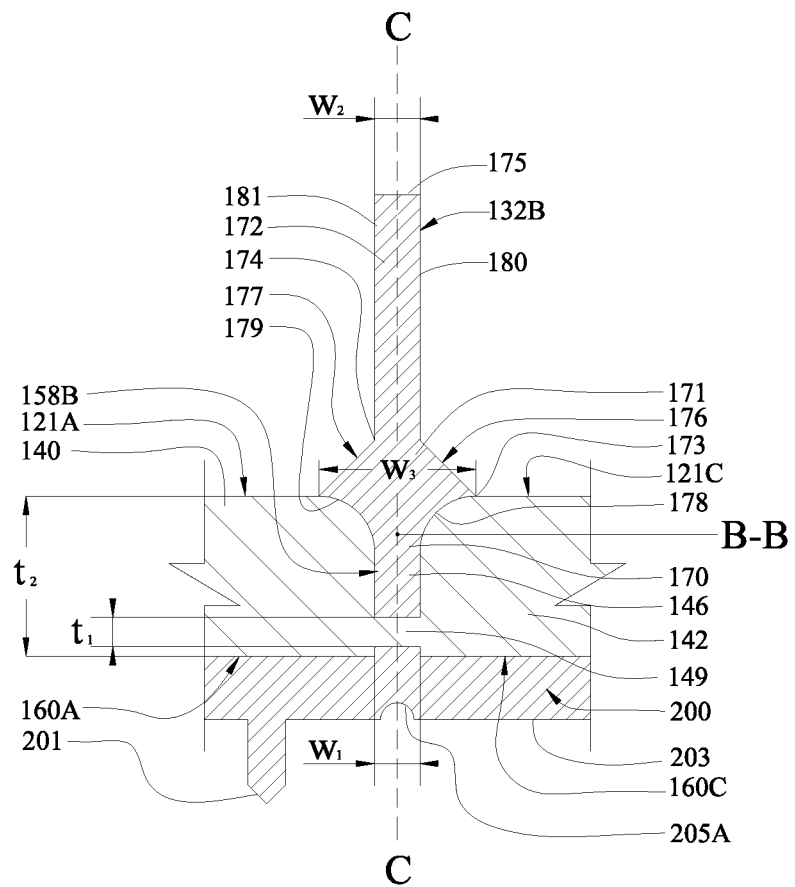
FIG. 12 is a cross-sectional view of the head of the toothbrush of FIG. 1 taken along line XII-XII of FIG. 11 wherein the segments are in a normal state.

The struts 148-152 are thin beam or thin shelf structures that extend between the peripheral segments 141-145 and the cruciform segment 140, thereby forming a flexible bridge therebetween. In one embodiment, the struts 148-152 are formed of a rigid material, such as a hard plastic, such as polypropylene. In a more specific embodiment, the struts 148-152 are formed of the same rigid material of which the segments 140-145 are formed, and possibly integrally formed therewith. While the struts 148-152 are constructed of what is considered a relatively rigid material in the art, flexibility of the struts 148-152 is still afforded by the thinned nature of the struts 148-152. For example, the struts 148-152 have a thickness $t_1$ (measured along an axis that is substantially perpendicular to the longitudinal axis A-A and passes through the front and rear surfaces) that is less than a thickness $t_2$ of the segments 140-145 (measured along an axis that is substantially perpendicular to the front surfaces 121A-F of the segments 140-145) (FIG. 12). In one embodiment, the ratio of $t_1:t_2$ is in a range of about 1:2 to about 1:5. Of course, the invention is not limited. When the channels 157-159B are filled with the elastomeric material 146, the struts 148-152 are encapsulated within the elastomeric material 146.

Referring again to FIGS. 6-10, each of the segments 140-145 further comprises at least one protuberance extending from a rear surface 160A-F of the segments 140-145. In the exemplified embodiment, cruciform segment 140 comprises five protuberances, namely two arcuate ridges 161A-B, a central post 162, and two protuberances 163-164. Of course, more or less protuberances can be used as desired. The peripheral segment 141 comprises the protuberance 169. The peripheral segment 142 comprises the protuberance 168. The distal segment 143 comprises the protuberance 167. The peripheral segment 144 comprises the protuberance 166. The peripheral segment 145 comprises the protuberance 165. As will be discussed in greater detail below, one of the purposes of one or all of the protuberances 161-169 is provide a contact surface for a mold used inject elastomeric material, in its liquid form, onto the skeleton 400 to fill the channels 157-159B, to form the elastomeric soft tissue cleaner 200, and to form the elastomeric cleaning elements 132A-E. Another purpose of one or all of the protuberances 161-169 is to provide an element that engages and/or scrapes soft oral tissue during use of the elastomeric soft tissue cleaner 200.

Referring now to FIGS. 4, 8, 10 and 12 concurrently, the oral care implement 100 further comprises an elastomeric soft tissue cleaner 200 located on the rear surface 122 of the head 120. The elastomeric soft tissue cleaner 200 is formed of an elastomeric material. The elastomeric material of the elastomeric soft tissue cleaner 200 may be any biocompatible resilient material suitable for uses in an oral hygiene apparatus. To provide optimum comfort as well as cleaning benefits, the elastomeric material preferably has a hardness property in the range of A8 to A25 Shore hardness. As an example, one preferred elastomeric material is styrene-ethylene/butylene-styrene block copolymer (SEBS) manufactured by GLS Corporation. Nevertheless, SEBS material from other manufacturers or other materials within and outside the noted hardness range could be used. In one embodiment, the elastomeric soft tissue cleaner 200 is integrally formed with the elastomeric material 146 of the channels 157-159B and the elastomeric cleaning elements 132A-E.

The elastomeric soft tissue cleaner 200 comprises a plurality of protuberances, in the form of nubs 201 and ridges 202, extending from a base surface 203 of the elastomeric soft tissue cleaner 200. As used herein a "nub" generally refers to a column-like protrusion (without limitation to the cross-sectional shape of the protrusion) which is upstanding from a base surface. In a general sense, the nub, in the preferred construction, has a height that is greater than the width at the base of the nub (as measured in the longest direction). Nevertheless, nubs could include projections wherein the widths and heights are roughly the same or wherein the heights are somewhat smaller than the base widths. Moreover, in some circumstances (e.g., where the nub tapers to a tip or includes a base portion that narrows to a smaller projection), the base width can be substantially larger than the height.

In one preferred arrangement of the elastomeric soft tissue cleaner 200, the nubs 201 are preferably conically shaped. As used herein, "conically shaped" or "conical" is meant to include true cones, frusto-conically shaped elements, and other shapes that taper to a narrow end and thereby resemble a cone irrespective of whether they are uniform, continuous in their taper, or have rounded cross-sections.

The protuberances 201, 202 of the elastomeric soft tissue cleaner 200 may help to significantly reduce a major source of bad breath in people and improve hygiene. The protuberances 201, 202 of the elastomeric soft tissue cleaner 200 enable removal of microflora and other debris from the tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise pulled against a tongue surface, the nubs 201 of the elastomeric tissue cleaner 200 provide for gentle engagement with the soft tissue while reaching downward into the recesses of adjacent papillae of the tongue. The ridges 202 of the elastomeric tissue cleaner 200 then scrape the soft oral tissue surface, thereby removing the dislodged debris. The elastomeric construction of the elastomeric soft tissue cleaner 200 also enables the base surface 203 to follow the natural contours of the oral tissue surfaces, such as the tongue, cheeks, lips, and gums of a user. Moreover, the nubs 201 and ridges 202 are able to flex as needed to traverse and clean the soft tissue surfaces in the mouth along which it is moved.

In one embodiment, the elastomeric soft tissue cleaner 200 overlies the rear surfaces 160A-F of the segments 140-145. The protuberances 161A-169 of the segments 140-145 extend through the elastomeric soft tissue cleaner 200. Thus, a portion of each of the protuberances 161A-169 remains exposed on the rear surface 122 of the head 120. In the exemplified embodiment, the protuberances 161A-B, 162 of the cruciform segment 140 are substantially flush with the base surface 203 of the elastomeric soft tissue cleaner 200. However, the protuberances 163-169 of the segments 140-145 extend beyond and, thus, protrude from the base surface 203 of elastomeric soft tissue cleaner 200.

Whether the protuberances 161A-169 are flush or protrude from the base surface 163 of the elastomeric soft tissue cleaner 200, the exposed portions of the protuberances 161A-169 provide contact surfaces for the mold during injection molding of elastomeric soft tissue cleaner 200 to the skeleton 400. By providing a protuberance 161A-169 having an exposed portion on each of the segments 140-145, each of the segments 140-145 can be maintained in a stable orientation during the injection molding process that flows the elastomeric material 146 into the channels 157-159B, forms the elastomeric soft tissue cleaner 200, and/or forms the elastomeric cleaning elements 132A-E. Furthermore, the protuberances 163-169 of the segments 140-145 that protrude from the base surface 203 of the elastomeric soft tissue cleaner 200 work in coordinated manner with the protuberances 201, 202 of the elastomeric soft tissue cleaner 200 to engage and clean soft oral tissue.

Referring now to FIGS. 4, 12, 14 and 16 concurrently, it can be seen that the elastomeric soft tissue cleaner 200 further comprises a plurality of grooves 204, 205A, 205B formed into the base surface 203. As discussed in grater detail below, the plurality of grooves 204, 205A are aligned with the channels 157-159B, which contain the elastomeric material 146. More specifically, the plurality of grooves 204, 205A-B are aligned with the channels 157-159B so that an axis that is perpendicular to the longitudinal axis A-A (such as axis C-C of FIG. 12) intersects both the channels 157-159B and the grooves 204, 205A-13.

Figure 14:
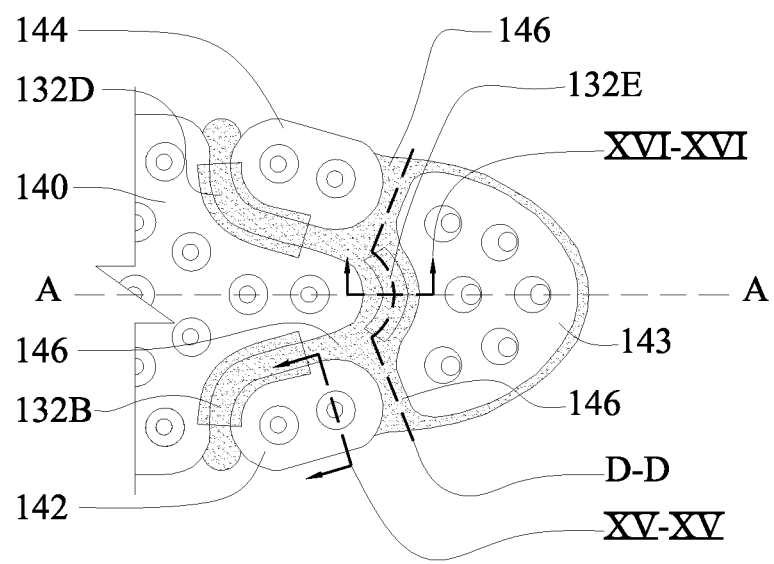
FIG. 14 is a dose-up view of the distal portion of the head of FIG. 5.
Figure 15:
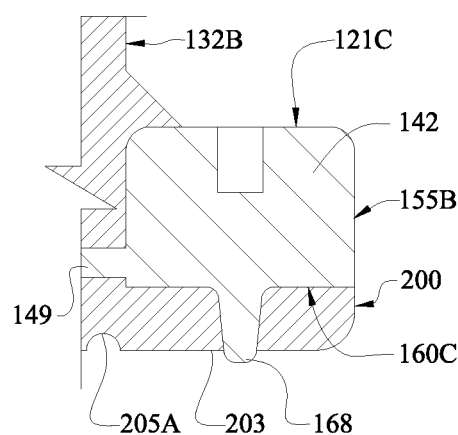
FIG. 15 is a cross-sectional view of the head of the toothbrush of FIG. 1 taken along line XV-XV of FIG. 14, wherein the segments are in a normal state.
Figure 16:
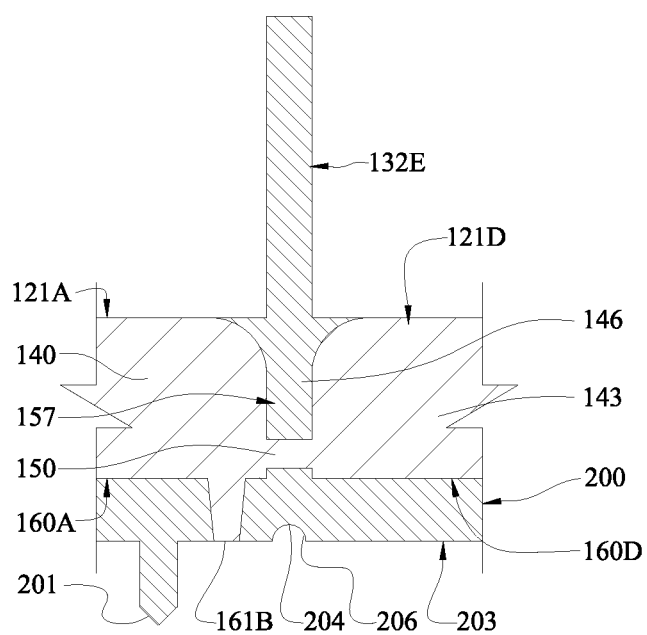
FIG. 16 is a cross-sectional view of the head of the toothbrush of FIG. 1 taken along line XVI-XVI of FIG. 14, wherein the segments are in a normal state.

In the exemplified embodiment, the elastomeric soft tissue cleaner 200 comprises a transverse groove 204 and two spaced-apart longitudinal grooves 205A, 205B. The transverse groove 204 extends transversely across the entire width of the head 120 from the right lateral edge 123 to the left lateral edge 124. The transverse groove 204 is aligned with the transverse channel 157 (best visible in FIG. 16). As a result, an axis that is perpendicular to the longitudinal axis A-A intersects both the transverse channel 157 and the transverse groove 204. As shown in FIGS. 12 and 14, the transverse channel 157 is nonlinear and extends generally along axis D-D. The transverse groove 204 also extends generally along axis D-D. The transverse groove 204 forms an upstanding transverse wall 206 that spans across the entire width of the head 120. This upstanding transverse wall 206 further assists with soft tissue cleaning when the elastomeric soft tissue cleaner 200 is dragged across a soft oral tissue by creating an additional scraping ridge. Moreover, the transverse nature of the groove 204 further assists during soft tissue cleaning by channeling fluid and dislodged debris to the lateral edges 123, 124 where it escapes from the elastomeric soft tissue cleaner 200 and does not become pressed back into the soft tissue. In addition to assisting with soft tissue cleaning, the transverse groove 204, by nature of being aligned with the transverse channel 157, also assist with tooth cleaning by providing an added amount of flexibility to the distal segment 143 relative to the cruciform segment 140.

The longitudinal grooves 205A, B extend longitudinally from the transverse groove 204 toward the proximal end 147 of the head 120, at the right and left lateral edges 123, 124 of the head 120 adjacent the proximal end 147. The longitudinal groove 205A is aligned with portions of both the channel 158B and the channel 159B (FIG. 12). The longitudinal groove 205B is aligned with portions of both the channel 158A and the channel 159A. Similar to the transverse groove 204, the longitudinal grooves 205A, B assist with soft tissue cleaning by channeling fluid and dislodged debris to the lateral edges 123, 124 where it escapes from the elastomeric soft tissue cleaner 200 and does not become pressed back into the soft tissue. The longitudinal channels 205A, B terminate at locations on the right and left lateral edges 123, 124 closer to the proximal end 147 of the head 120 than does the transverse groove 204 such that the fluids and debris are dispensed at different locations so as to prevent clogging. Moreover, by nature of being aligned with the channels 158B, 159B, the longitudinal groove 205A assists with tooth cleaning by providing an added amount of flexibility to the peripheral segments 141, 142 relative to the cruciform segment 140. Similarly, by nature of being aligned with the channels 158A, 159A, the longitudinal groove 205B assists with tooth cleaning by providing an added amount of flexibility to the peripheral segments 144, 145 relative to the cruciform segment 140

Figure 11:
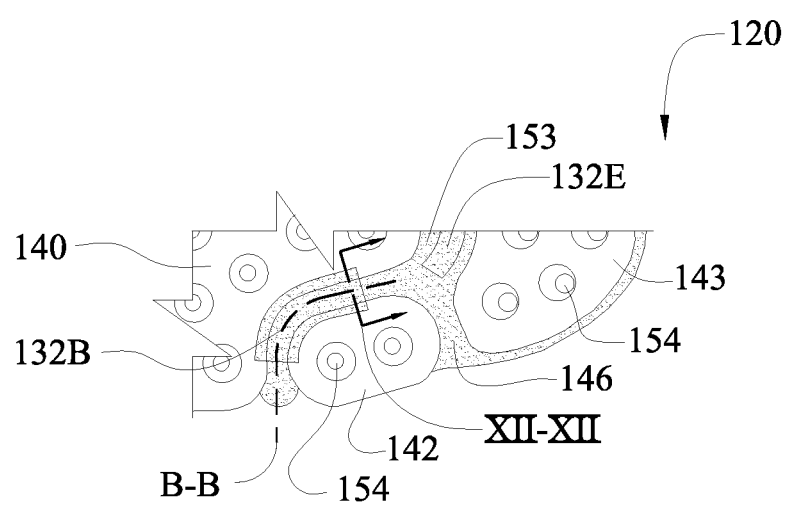
FIG. 11 is a close-up view of a quadrant of the head of FIG. 5.

Referring now to FIGS. 3, 11 and 12 concurrently, one embodiment of an elastomeric cleaning element and its structural cooperation with the head 120 will be described. For purposes of discussion, the following description will refer to the elastomeric cleaning element 132B as an elastomeric wall 132B because the exemplified embodiment depicts a wall. While the embodiment of the elastomeric cleaning element will be described in relation to the elastomeric wall 132B and its interaction with the channel 158B and the elastomeric material 146 contained therein, it is to be understood that the discussion below is applicable to the other elastomeric walls 132A, 132C, 132D and their interaction with the channels 159B, 159A, 158A and the elastomeric material 146 contained therein. Moreover, while the invention will be discussed in terms of an elastomeric wall, it is to be understood that the principles discussed below could be applied to elastomeric fingers and other elastomeric structures in other embodiments.

Figure 13:
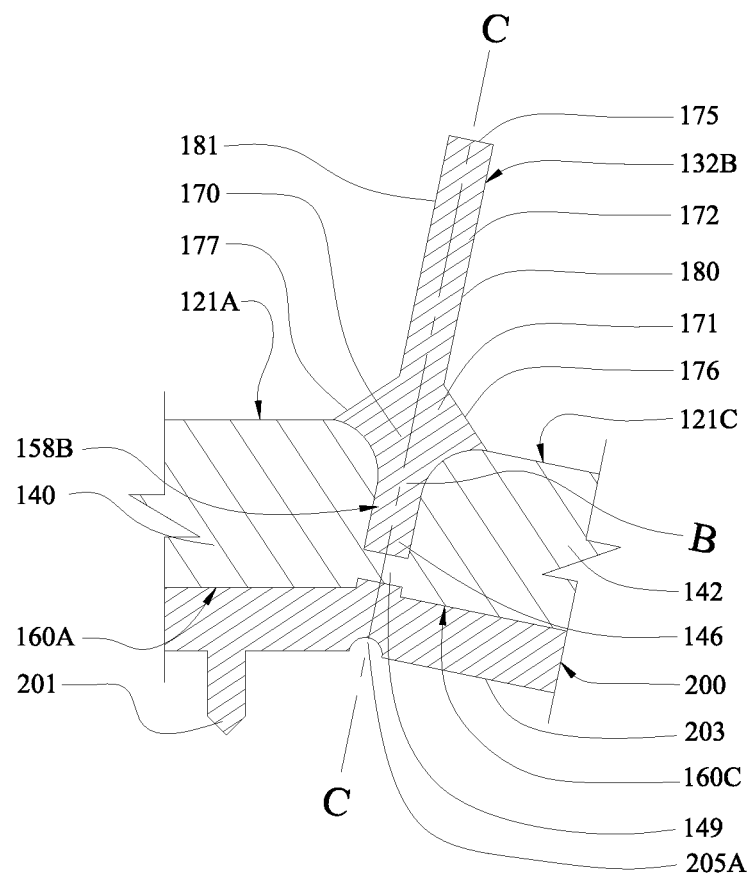
FIG. 13 is a cross-sectional view of the head of the toothbrush of FIG. 1 taken along line XII-XII of FIG. 11, wherein the segments are in a flexed state.

The elastomeric wall 132B is an arcuate wall that extends along the curved channel 158B. More specifically, the channel 158B extends along curved axis B-B. In the exemplified embodiment, the elastomeric wall 132B also extends along the curved axis B-B and extends upward from the front surface 121 of the head 120 along, an axis C-C. In FIG. 12, the segments 140, 142 of the bead 120 are in a normal state (i.e., a state in which no forces are applied to the head 120). In the normal state, the segments 140, 142 are not flexed relative to one another and the surfaces 121A, 121C of the segments are substantially coplanar. In FIG. 13, the segments 140, 142 of the head 120 are in a flexed state (i.e., a state in which forces imparted during normal brushing are applied to the head 120). In the flexed state, the segments 140, 142 are flexed relative to one another so that the front surfaces 121A, 121C are moved into a non-coplanar arrangement. Upon cessation of brushing forces, the elastomeric material 146 of the channel 158B and the strut 149 bias the segments 140, 142 back into the normal state. The invention, however, is not limited to instances where the front surfaces 121A, 121C are in a coplanar arrangement in the normal state and flexed into a non-coplanar arrangement in the flexed state. In certain alternative embodiments, the front surfaces 121A, 121C could be in a non-coplanar arrangement in the normal state and flexed into a arrangement in the flexed state. In still another alternative embodiment, the front surfaces 121A, 121C could be in a first non-coplanar arrangement (i.e., at a first angle relative to one another) in the normal state and flexed into a second non-coplanar arrangement (i.e., at a second different angle relative to one another) in the flexed state. It is contemplated that the arrangement of the front faces 121A, 121C in the normal state and the flexed state can be altered, if desired.

Referring to FIG. 12, the elastomeric wail 132B generally comprises a root portion 170, a base portion 171 and an upper portion 172. The root portion 170 is disposed within the channel 158B and connected to the elastomeric material 146 within the channel 158B. The root portion 170 extends upward from the elastomeric material 146 along an axis C-C and connects to a lower end 173 of the base portion 171. The base portion 171 extends upward along the axis C-C from the lower end 173 to an upper end 174. The upper portion 172 of the elastomeric wall 132B extends upward along the axis C-C from the upper end 174 of the base portion 171 to a terminal end 175. In the exemplified embodiment, the terminal end 175 is flat. However, in other embodiments, the terminal end 175 can be rounded or tapered, or be in the form of other suitable shapes.

The lower end 173 of the base portion 171 of the elastomeric wall 132B has a width $W_3$, measured perpendicular to the axis B-B. The upper end 174 of the base portion 171 of the elastomeric wall 132B has a width $W_2$, measured perpendicular to the axis B-B. The width $W_2$ is less than the width $W_3$. The width $W_3$ of the lower end 173 of the base portion 171 of the elastomeric wall 132B is greater than the width $W_1$ of the channel 158B, measured perpendicular to the axis B-B. As a result of the width $W_3$ being greater than the width $W_1$, the lower end 173 of the base portion 171 overlies portions 178, 179 of the front surfaces 121C, 121A of the segments 142, 140 respectively. The remainder of the front surfaces 121C, 121A of the segments 142, 140 remain exposed.

In the exemplified embodiment, the base portion 171 comprises two oblique surfaces 176, 177 and, thus, the base portion 171 gradually tapers in width from the lower end 173 to the upper end 174. In alternate embodiments, the base portion 171 may include stepped surfaces rather than the two oblique surfaces 176, 177. In such an embodiment, the base portion 171 would taper in a stepped manner rather than gradually.

The upper portion 172 of the elastomeric wall 132B comprises a first major surface 180 and a second major surface 181 that is opposite to the first major surface 180, in the exemplified embodiment, the first and second major surfaces 180, 181 are substantially parallel to one another, thereby resulting in the upper portion 172 having a constant width $W_2$ along its height. In certain embodiments, the width $W_2$ will be equal to or less than the width $W_1$ of the channel 158B. In one specific embodiment, the width $W_2$ may be substantially equal to the width $W_1$ of the channel 158B.

By designing the elastomeric wall 132B so that the base portion 171 is wider than the upper portion 172, the upper portion 172 remains flexible so that it can wipe the surfaces of teeth. However, the base portion 171 will provide structural integrity and helps prevent excessive wear/bending of the elastomeric wall 132B. Moreover, by connecting the lower end 173 of the base portion 171 to the portions 178, 179 of the front surfaces 121C, 121A of the segments 142, 140, the elastomeric wall 132B will assist in preventing over-flexing of the segments 142, 140 relative to one another while being imparted with extra motion induced by said limited flexing between the segments 142, 140.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An oral care implement comprising:
   a handle;
   a head connected to the handle, the head formed by a plurality of segments constructed of a rigid material, the plurality of segments including a first segment and a second segment, each of the first and second segments comprising a front surface, wherein the first and second segments are spaced apart so that a channel exists between the first and second segments;
   an elastomeric material in the channel connecting the first and second segments, the first and second segments being flexible relative to one another between a normal state and a flexed state; and
   an elastomeric cleaning element comprising: a base portion connected to and extending from the elastomeric material disposed in the channel, the base portion overlying a portion of each of the front surfaces of the first and second segments when the first and second segments are in the normal state; and an upper portion extending from the base portion;
   wherein the elastomeric cleaning element is an elastomeric wall, the upper portion of the elastomeric cleaning element comprising a first major surface and a second major surface opposite the first major surface, the first and second major surfaces being substantially parallel to one another, the base portion of the elastomeric cleaning element comprising a first surface that extends obliquely from the first major surface and a second surface that extends obliquely from the second major surface.

2. The oral care implement according to claim 1 wherein the base portion is a tapered base portion, such that the tapered base portion of the elastomeric cleaning element extends from a lower end adjacent the top surfaces of the first and second segments to an upper end, the upper portion of the elastomeric cleaning element extending from the upper end of the tapered base portion, and wherein the lower end has a first width that is greater than a width of the channel.

3. The oral care implement according to claim 2 wherein the upper end of the tapered base portion has a second width that is equal to or less than the width of the channel.

4. The oral care implement according to claim 3 wherein the upper portion of the elastomeric cleaning element has a substantially constant width that is substantially equal to the second width.

5. The oral care implement according to claim 2 wherein the tapered base portion of the elastomeric cleaning element is connected to the portions of the front surfaces of the first and second segments that are overlaid by the tapered base portion.

6. The oral care implement according to claims 1 wherein the channel extends along a curved axis, the elastomeric wall being arcuate and extending along the curved axis of the channel.

7. The oral care implement according to claim 1 wherein the elastomeric cleaning element further comprises a root portion disposed within the channel, the root portion connected to and extending from the elastomeric material of the channel to the base portion.

8. The oral care implement according to claim 1 wherein the front surfaces of each of the first and second segments comprise a bristle region comprising at least one bristle tuft extending therefrom.

9. The oral care implement of claim 8 wherein the bristle regions of the front surfaces of the first and second segments are formed by exposed portions of the rigid material.

10. The oral care implement according to claim 1 further comprising at least one strut positioned in the channel and extending between the first and second segments, the strut formed of the rigid material.

11. The oral care implement according to claim 10 wherein the strut is integrally formed with the first and second segments.

12. The oral care implement according to claim 10 wherein the strut has a first thickness and the first and second segments have a second thickness, wherein the first thickness is less than the second thickness.

13. The oral care implement according to claim 10 wherein the strut is encapsulated in the elastomeric material of the channel.

14. The oral care implement according to claim 1 wherein the elastomeric cleaning element is integrally formed with the elastomeric material of the channel.

15. The oral care implement according to claim 1 wherein the elastomeric cleaning element is integrally formed with the elastomeric material of the channel, the elastomeric material of the channel being a thermoplastic elastomer and the rigid material being a hard plastic.

16. The oral care implement according to claim 1 wherein when in the normal state, the front surfaces of the first and second segments are substantially coplanar with one another; and when in the flexed state, the front surfaces of the first and second segments are non-coplanar with one another.

17. An oral care implement comprising:
   a handle;
   a head connected to the handle, the head formed by a plurality of segments constructed of a rigid material, the plurality of segments including a first segment and a second segment, each of the first and second segments comprising a front surface, wherein the first and second segments are spaced apart so that a channel exists between the first and second segments;
   an elastomeric material in the channel connecting the first and second segments, the first and second segments being flexible relative to one another between a normal state and a flexed state;
   an elastomeric cleaning element comprising: a base portion connected to and extending from the elastomeric material disposed in the channel, the base portion overlying a portion of each of the front surfaces of the first and second segments when the first and second segments are in the normal state; and an upper portion extending from the base portion; and an elastomeric soft tissue cleaner located on a rear surface of the head opposite the front surfaces of the first and second segments, the elastomeric soft tissue cleaner comprising a plurality of protuberances for engaging soft oral tissue and being integrally formed with the elastomeric material of the channel.

18. An oral care implement comprising:

a handle;

a head connected to the handle, the head formed by a plurality of segments constructed of a rigid material, the plurality of segments including a first segment and a second segment, each of the first and second segments comprising a front surface, wherein the first and second segments are spaced apart so that a channel exists between the first and second segments, the channel extending along an axis and having a width measured perpendicular to said axis;

an elastomeric material in the channel connecting the first and second segments; and an elastomeric cleaning element comprising: a base portion connected to and extending from the elastomeric material disposed in the channel, the base portion extending from a lower end that overlies a portion of each of the front surfaces of the first and second segments to an upper end spaced from the front surfaces of the first and second segments; and an upper portion extending from the upper end of the base portion to a terminal end, the lower end of the base portion having a first width measured perpendicular to the axis of the channel that is greater than the width of channel, the upper end of the base portion having a second width measured perpendicular to the axis of the channel that is less than the first width;

wherein the elastomeric cleaning element is an elastomeric wall, the upper portion of the elastomeric cleaning element comprises a first major surface and a second major surface opposite the first major surface, the first and second major surfaces being substantially parallel to one another, the base portion of the elastomeric cleaning element comprising a first surface that extends obliquely from the first major surface and a second surface that extends obliquely from the second major surface.

19. The oral care implement according to claim 18 wherein the upper portion of the elastomeric cleaning element has a substantially constant third width from the upper end of the base portion to the terminal end, the third width measured perpendicular to the axis of the channel.

20. The oral care implement according to claim 18 wherein the terminal end is rounded or tapered.

21. The oral are implement according to claim 18 wherein the first and second segments are flexible relative to one another between a normal state in which the front surfaces of the first and second segments are substantially coplanar with one another and a flexed state in which the front surfaces of the first and second segments are non-coplanar with one another.

22. The oral care implement according to claim 18 wherein the axis of the channel is curved, the elastomeric wall being arcuate and extending along the curved axis of the channel.

23. The oral care implement according to claim 18 wherein the elastomeric cleaning element further comprises a root portion disposed within the channel, the root portion connected to and extending from the elastomeric material of the channel to the lower end of the base portion.

24. The oral care implement according to claim 18 wherein the lower end of the base portion of the elastomeric cleaning element is connected to the portions of the front surfaces of the first and second segments that are overlaid by the lower end of the base portion.

25. The oral care implement according to claim 18 wherein the front surfaces of each of the first and second segments comprise a bristle region comprising at least one bristle tuft extending therefrom.

26. The oral care implement according to claim 25 wherein the bristle regions of the front surfaces of the first and second segments are formed by exposed portions of the rigid material.

27. The oral care implement according to claim 18 further comprising at least one strut positioned in the channel and extending between the first and second segments, the strut formed of the rigid material.

28. The oral care implement according to claim 27 wherein the strut is integrally formed with the first and second segments, the strut having a first thickness and the first and second segments have a second thickness, wherein the first thickness is less than the second thickness.

29. The oral care implement according to claim 18 wherein the elastomeric cleaning element is integrally formed with the elastomeric material of the channel.

30. The oral care implement according to claim 18 further comprising an elastomeric soft tissue cleaner located on a rear surface of the head opposite the front surfaces of the first and second segments, the elastomeric soft tissue cleaner comprising a plurality of protuberances for engaging soft oral tissue and being integrally formed with the elastomeric material of the channel.

31. An oral care implement comprising:

a handle;

a head connected to the handle, the head having a front surface and at least one channel in the front surface of the head, the channel extending along an axis; and an elastomeric wall extending from the front surface of the head, the elastomeric wall comprising: a root portion disposed within the channel; a tapered base portion connected to and extending from the root portion, the tapered base portion overlying portions of the front surface of the head on opposite sides of the channel; and an upper portion extending from the tapered base portion to a terminal end;

wherein the upper portion of the elastomeric cleaning element comprises a first major surface and a second major surface opposite the first major surface, the first and second major surfaces being substantially parallel to one another, the tapered base portion of the elastomeric cleaning element comprising a first surface that extends obliquely from the first major surface and a second surface that extends obliquely from the second major surface.

32. The oral care implement according to claim 31 wherein the tapered base portion of the elastomeric wall extends from a lower end adjacent the top surface of the head to an upper end, the upper portion extending upward from the upper end of the tapered base portion, and the root portion extending downward from the lower end of the tapered base portion.

33. The oral care implement according to claim 31 wherein the terminal end of the upper portion of the elastomeric wall is rounded or tapered.

34. The oral care implement according to claim 31 wherein the axis of the channel is curved, the elastomeric wall being arcuate and extending along the curved axis of the channel.

35. The oral care implement according to claim 31 wherein the tapered base portion of the elastomeric cleaning element is connected to the portions of the front surfaces of the head that are overlaid by the tapered base portion.

* * * * *

UNITED STATES PATENT AND TRADEMARK OFFICE
CERTIFICATE OF CORRECTION

PATENT NO.      : 9,027,193 B2
APPLICATION NO. : 13/992263
DATED           : May 12, 2015
INVENTOR(S)     : Wen Jin Xi, Yu Liu and Jian Rong Zhou It is certified that error appears in the above-identified patent and that said Letters Patent is hereby corrected as shown below:

On the Title page, item (75), in the listing of Inventors, delete "Liu Yu" and replace it with --Yu Liu--.

Signed and Sealed this
Eighteenth Day of August, 2015

Michelle K. Lee
*Director of the United States Patent and Trademark Office*